(12) United States Patent
Nagashima

(10) Patent No.: US 11,202,724 B2
(45) Date of Patent: Dec. 21, 2021

(54) ABSORBENT ARTICLE

(71) Applicant: DAIO PAPER CORPORATION, Ehime (JP)

(72) Inventor: Mariko Nagashima, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 617 days.

(21) Appl. No.: 16/083,087

(22) PCT Filed: Mar. 24, 2017

(86) PCT No.: PCT/JP2017/012004
§ 371 (c)(1),
(2) Date: Sep. 7, 2018

(87) PCT Pub. No.: WO2017/170222
PCT Pub. Date: Oct. 5, 2019

(65) Prior Publication Data
US 2019/0060139 A1 Feb. 28, 2019

(30) Foreign Application Priority Data
Mar. 29, 2016 (JP) .............................. JP2016-065245

(51) Int. Cl.
*A61F 13/511* (2006.01)
*A61F 13/47* (2006.01)
(Continued)

(52) U.S. Cl.
CPC .. *A61F 13/51108* (2013.01); *A61F 13/15617* (2013.01); *A61F 13/47* (2013.01);
(Continued)

(58) Field of Classification Search
CPC ......................... A61F 13/51108; A61F 13/511; A61F 13/539; A61F 13/537; A61F 13/512;
(Continued)

(56) References Cited

U.S. PATENT DOCUMENTS 10,071,000 B2 * 9/2018 Umemoto .......... A61F 13/51108
10,092,463 B2 * 10/2018 Nomoto ............ A61F 13/51113
(Continued)

FOREIGN PATENT DOCUMENTS

| CN | 101892557 A | 11/2010 |
|---|---|---|
| CN | 103826584 A | 5/2014 |

(Continued)

OTHER PUBLICATIONS

International Search Report dated Jun. 13, 2017 of corresponding application No. PCT/JP2017/012004; 1 pg.
(Continued)

*Primary Examiner* — Michele M Kidwell
(74) *Attorney, Agent, or Firm* — Maier & Maier, PLLC

(57) ABSTRACT

A water repellent is applied to a spun lace nonwoven fabric in which a surface sheet comprises 100% by weight of cotton fibers, and a large number of openings that penetrate the obverse and reverse surfaces are formed in at least a portion that corresponds to an excretory opening. A heat-fusible fiber sheet is disposed adjacent to the absorber side surface of the surface sheet. A plurality of adhesive portions are formed between the surface sheet and the heat-fusible fiber sheet along the longitudinal direction and spaced apart in the widthwise direction of an incontinence pad. A compressed groove recessed from the outer surface of the surface sheet toward the absorber is formed close to the adhesive portions.

8 Claims, 10 Drawing Sheets

(51) Int. Cl.
    *A61F 13/539*     (2006.01)
    *A61L 15/28*     (2006.01)
    *A61F 13/537*     (2006.01)
    *A61F 13/512*     (2006.01)
    *A61F 13/15*     (2006.01)

(52) U.S. Cl.
    CPC .......... *A61F 13/511* (2013.01); *A61F 13/512* (2013.01); *A61F 13/51121* (2013.01); *A61F 13/537* (2013.01); *A61F 13/539* (2013.01); *A61L 15/28* (2013.01); *A61F 2013/15934* (2013.01); *A61F 2013/4708* (2013.01)

(58) Field of Classification Search
    CPC ................ A61F 13/51121; A61F 13/47; A61F 13/15617; A61F 2013/15934; A61F 2013/4708
    See application file for complete search history.

(56) References Cited

U.S. PATENT DOCUMENTS

| | | | | |
|---|---|---|---|---|
| 10,195,090 | B2* | 2/2019 | Kurihara | A61F 13/15707 |
| 10,342,716 | B2* | 7/2019 | Tagomori | A61F 13/15 |
| 10,555,843 | B2* | 2/2020 | Suzuki | A61F 13/51108 |
| 10,596,044 | B2* | 3/2020 | Umemoto | A61F 13/15707 |
| 10,806,642 | B2* | 10/2020 | Tagomori | A61F 13/4753 |
| 2004/0162536 | A1* | 8/2004 | Becker | A61F 13/15203 |
| | | | | 604/367 |
| 2012/0226250 | A1* | 9/2012 | Sato | A61F 13/51104 |
| | | | | 604/367 |
| 2017/0258647 | A1* | 9/2017 | Orr | B32B 7/12 |
| 2019/0053958 | A1* | 2/2019 | Kurihara | A61F 13/537 |

FOREIGN PATENT DOCUMENTS

| | | |
|---|---|---|
| EP | 1 290 995 A2 | 3/2003 |
| JP | 2009-148328 A | 7/2009 |
| JP | 2010-279604 A | 12/2010 |
| JP | 2011-255023 A | 12/2011 |
| JP | 2013-66614 A | 4/2013 |
| KR | 1020100126197 A | 12/2010 |
| WO | 2014204016 A1 | 12/2014 |

OTHER PUBLICATIONS

Extended European Search Report dated Mar. 4, 2019, in connection with corresponding EP Application No. 17774759.9; 8 pages.
Chinese Office Action dated Jun. 9, 2020, in connection with corresponding CN Application No. 201780015667.0 (17 pp., including machine-generated English translation).
Chinese Office Action dated Dec. 15, 2020, in connection with corresponding CN Application No. 201780015667.0 (17 pp., including machine-generated English translation).
Chinese Office Action dated Apr. 1, 2021, in connection with corresponding CN Application No. 201780015667.0 (10 pp., including machine-generated English translation).
Taiwanese Office Action dated May 8, 2020, in connection with corresponding TW Application No. 106108903 (12 pp., including machine-generated English translation).

\* cited by examiner

[FIG. 1]
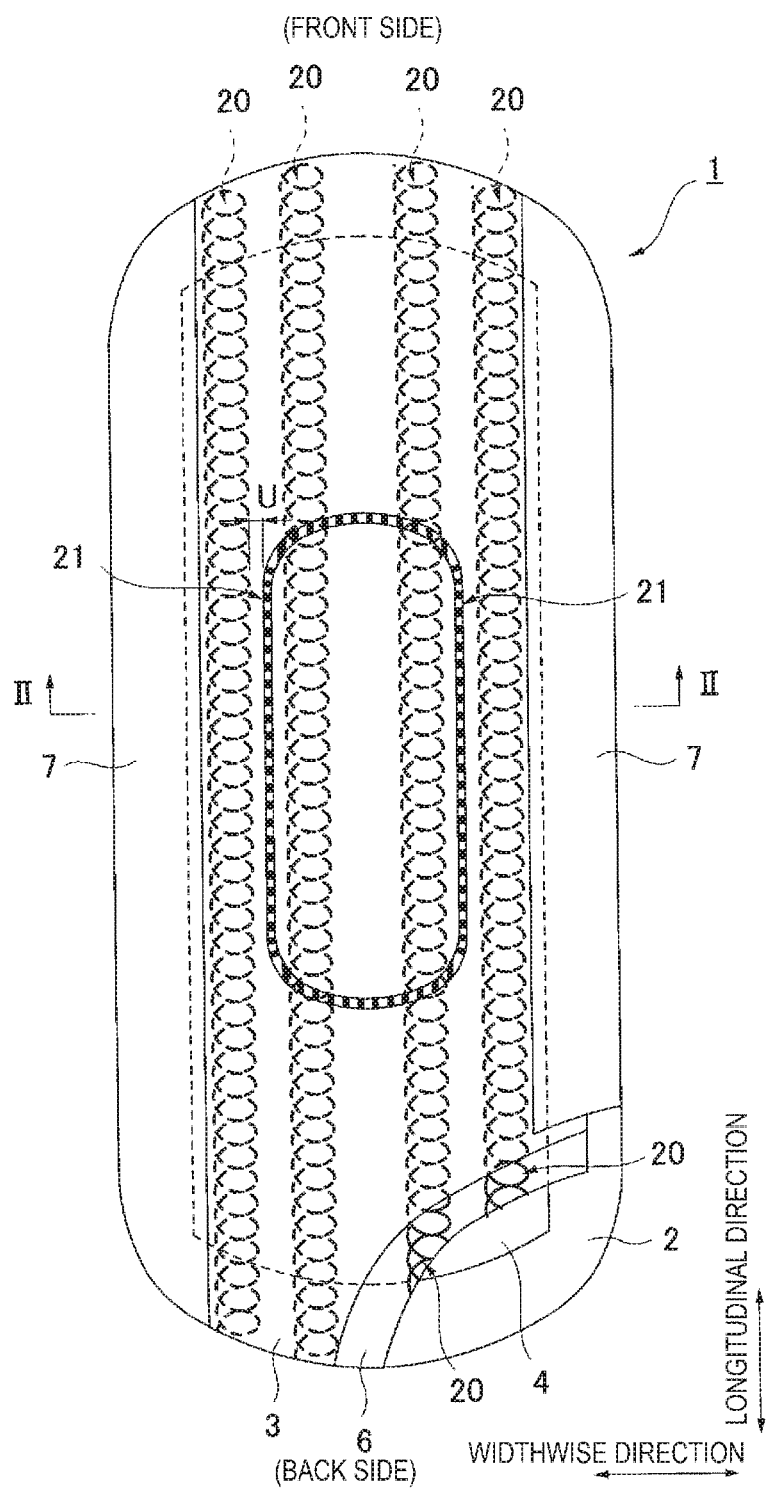

[FIG. 2]
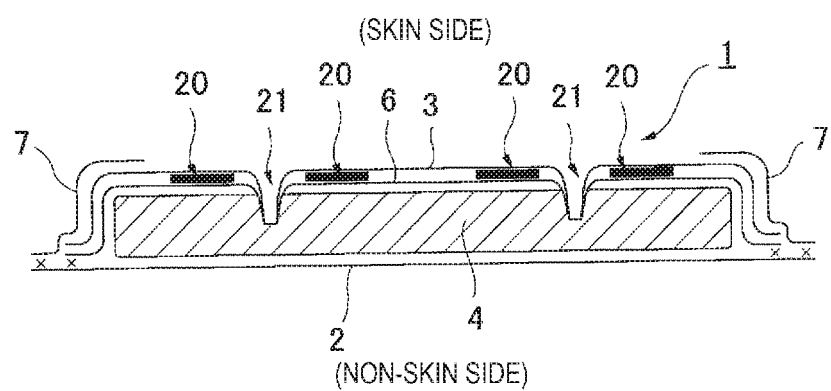
[FIG. 3]
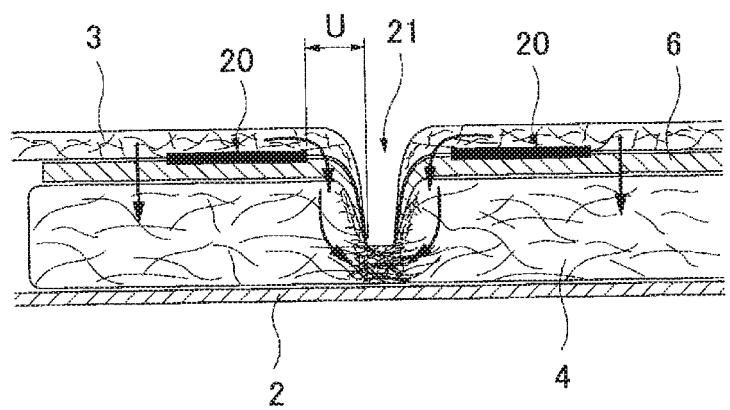

[FIG. 4]
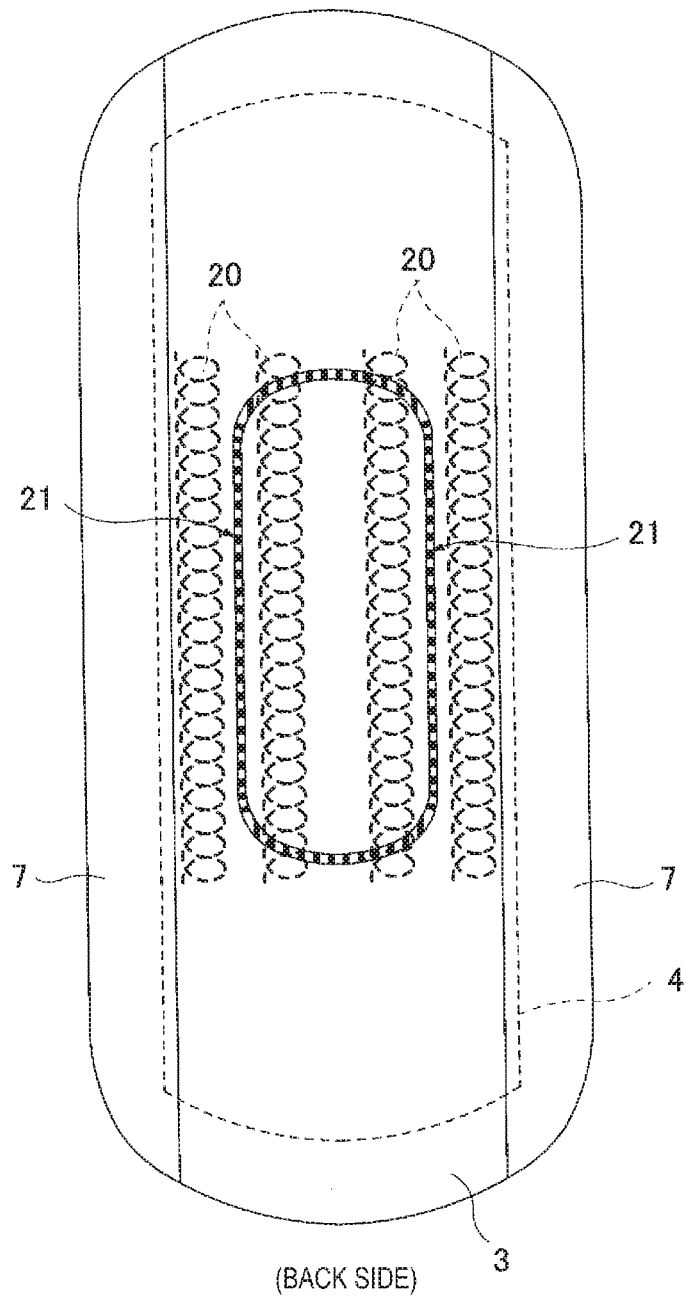

[FIG. 5]
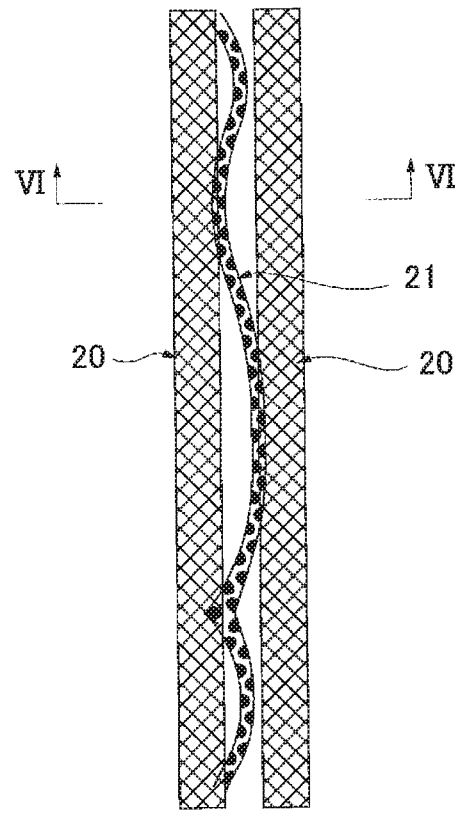
[FIG. 6]
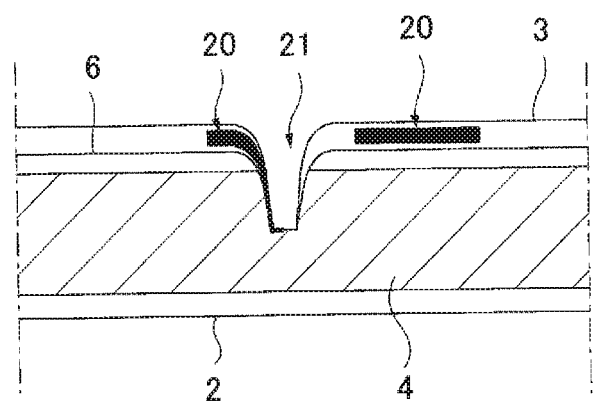

[FIG. 7]
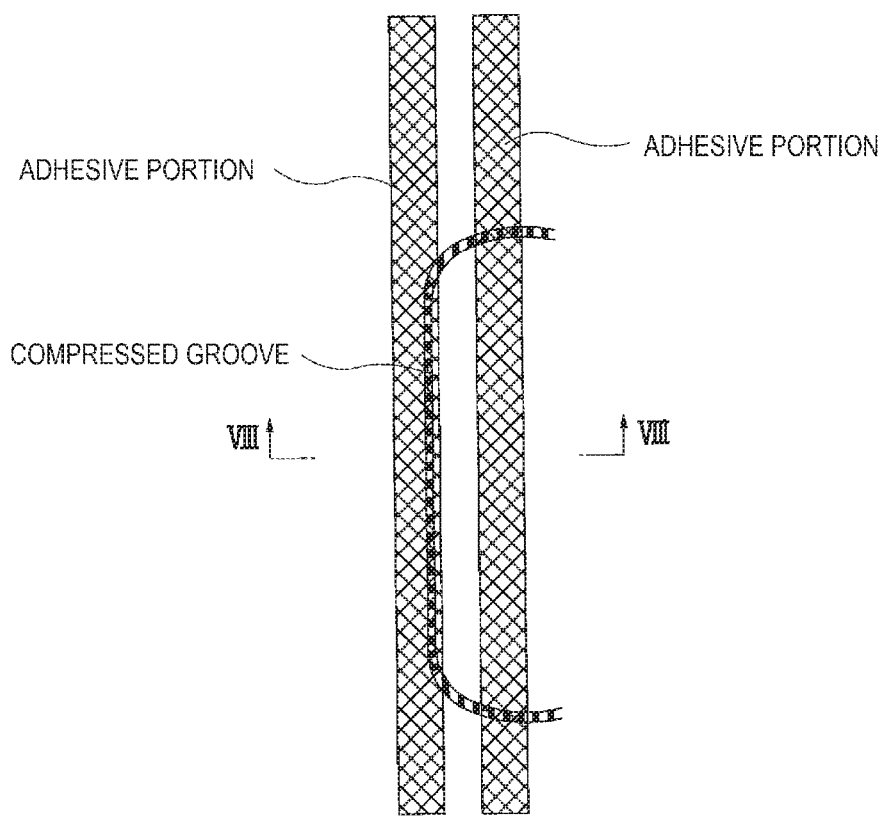
[FIG. 8]
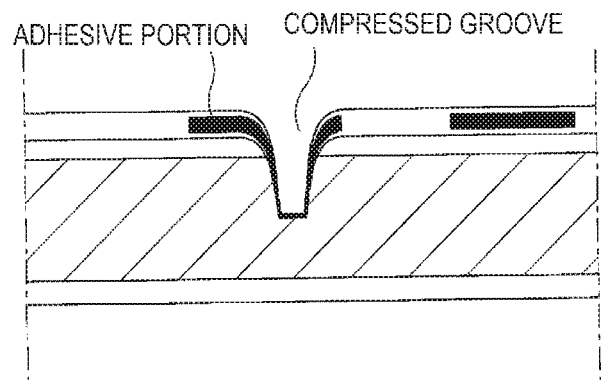

[FIG. 9]
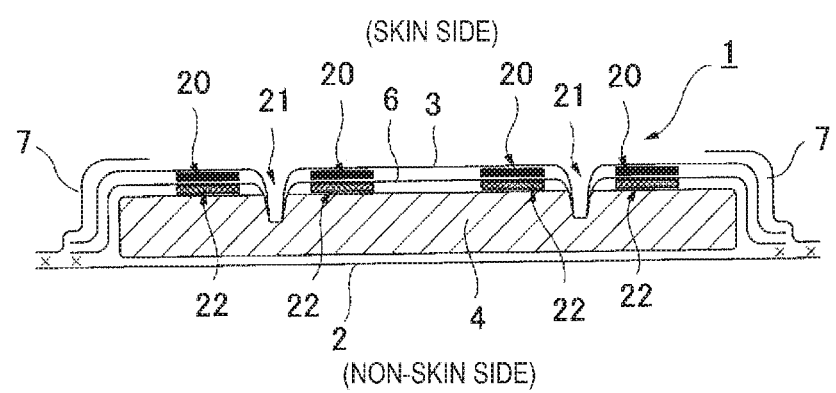

[FIG. 10]
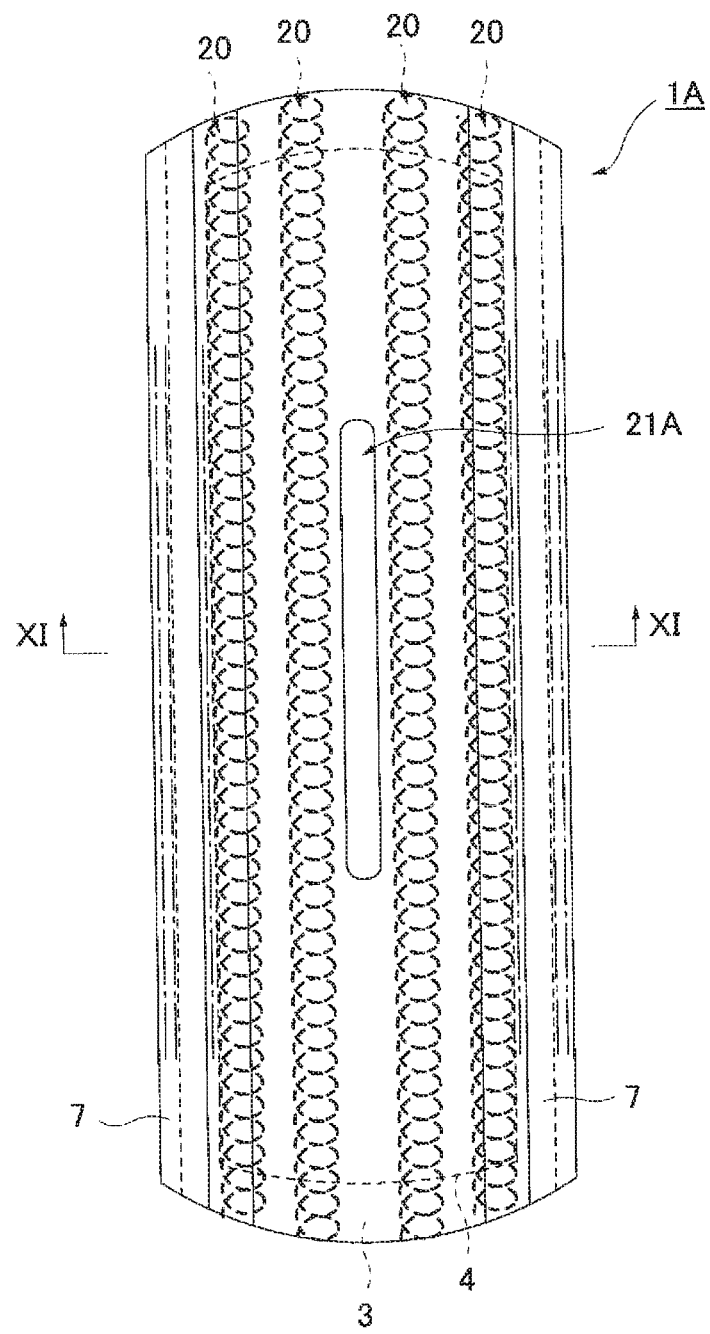

[FIG. 11]
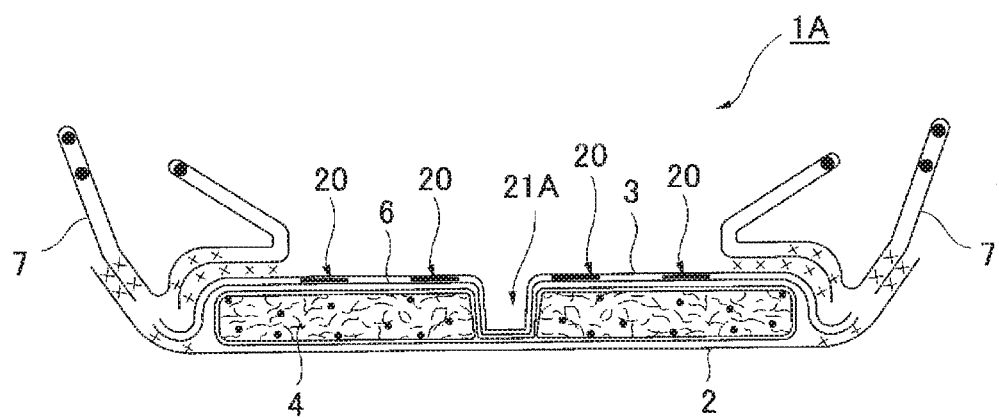

[FIG. 12]
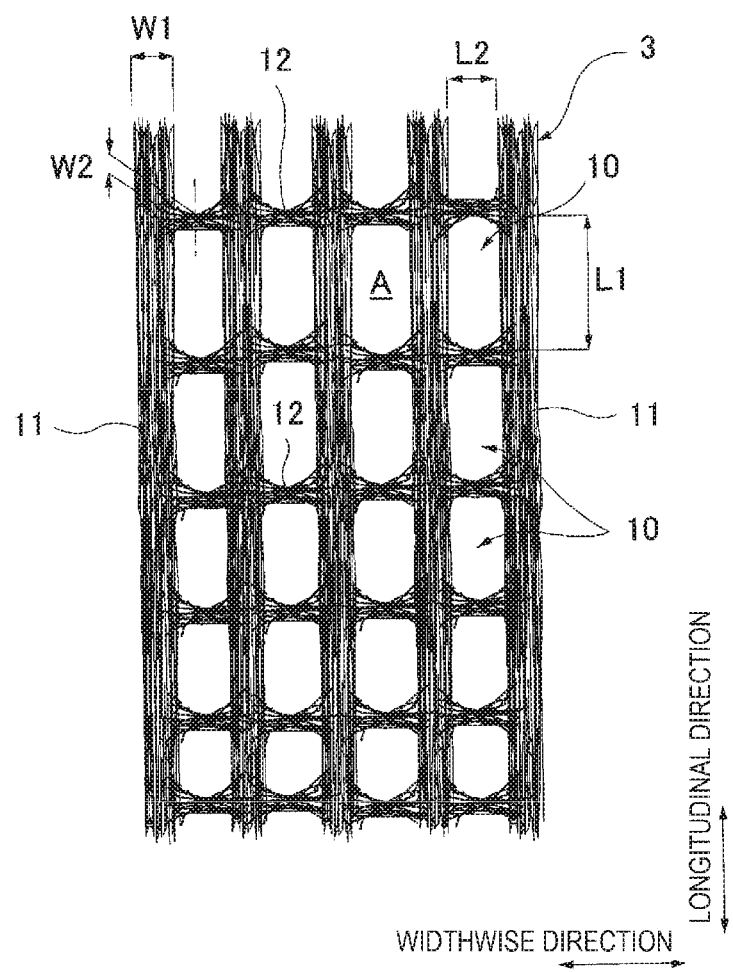

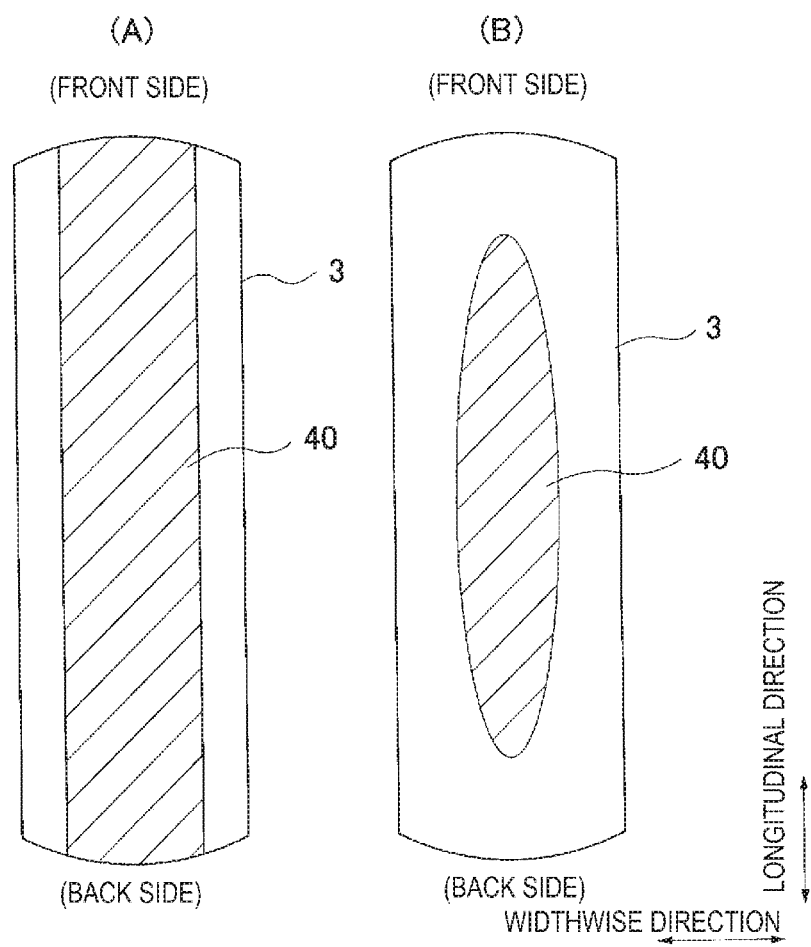
[FIG. 13]

ABSORBENT ARTICLE

FIELD

The present invention relates to an absorbent article mainly used for an incontinence pad, and specifically relates to an absorbent article using cotton nonwoven fabric as a surface sheet.

BACKGROUND

Conventionally, an absorbent article in which an absorber made of cotton-like pulp, etc. is interposed between a surface sheet and a liquid impermeable back sheet such as a polyethylene sheet or a polyethylene sheet laminated nonwoven fabric has been known as an absorbent article for women such as an incontinence pad, a panty liner (Pantyliner), or a sanitary napkin.

The surface sheet forms a skin-contact surface, and thus is required to be flexible, obtain a dry feel even after absorption of an excreted liquid, and cause little irritation to a skin. As a material satisfying such requirements, a nonwoven fabric of synthetic fibers and a resin mesh sheet have been widely adopted in a field of absorbent articles, particularly in a field of incontinence pads. However, there has been a problem that a surface sheet made of a synthetic fiber causes itching, rash, etc.

As a solution to this problem, a surface sheet made of cotton fiber (cotton) has been proposed. However, in an absorbent article, a surface sheet has high liquid permeability, and it is desired that a liquid be allowed to rapidly reach an absorber. However, when an ordinary absorbent cotton fiber is contained in the surface sheet, there is a problem that the surface sheet has a high liquid retaining property and a sticky feeling tends to remain on the surface.

In addition, while the absorbent article in which the surface sheet is made of cotton fiber has an advantage that a soft tactile property can be realized as in underwear, the absorbent article has a high liquid retaining property as described above. Thus, when a large amount of body fluid is discharged, the body fluid remains on the surface sheet and causes stuffiness, rash, etc. due to wearing for a long time. For this reason, in a conventional absorbent article, using cotton fiber as a surface sheet is limited to a product that requires less absorption of a body fluid such as a panty liner.

Focusing on flexibility of such a cotton nonwoven fabric, application of an absorbent article to a surface sheet has been studied as shown in Patent Documents 1 and 2 below. Patent Document 1 below discloses an absorbent article in which a surface sheet located on a skin-facing surface and containing non-thermally melting fiber is included, a pair of side sheets disposed on the skin-facing surface of the surface sheet and spaced apart in a lateral direction and a thermally melting sheet disposed between the surface sheet and an absorber to overlap with the side sheets through the surface sheet are included, the side sheets and the thermally melting sheet are formed by synthetic fiber containing thermoplastic resin, and a welding portion that joins the side sheets and the thermoplastic sheet together by thermal melting through the surface sheet is formed between the side sheets and the thermoplastic sheet.

In addition, Patent Document 2 discloses an absorbent article in which a surface sheet includes a cotton nonwoven fabric, a heat-fusible fiber sheet having a lower fiber density than that of the cotton nonwoven fabric and having hydrophilicity is located below the surface sheet and interposed between the surface sheet and an absorber, and embossment is performed a plurality of times from a surface side in these laminated states.

Patent Document 1: JP-A-2013-66614
Patent Document 2: JP-A-2009-148628

SUMMARY

However, in the absorbent article described in the above Patent Document 1, the surface sheet and the thermally melting sheet disposed on the absorber side thereof are joined only at both side portions of the surface sheet with which the side sheets overlap. In the absorbent article described in the above Patent Document 2, the surface sheet and the heat-fusible fiber sheet disposed on the absorber side thereof are attached to each other only in a portion subjected to heat sealing embossment. Thus, detachment of the surface sheet generating a gap between the surface sheet and a sheet on a lower layer side is likely to occur in a non-joined portion between the surface sheet and the sheet on the lower layer side, and there is a problem that a body fluid is hardly transferred from the surface sheet to the sheet on the lower layer side. As a result, there is concern that a liquid may remain on the surface sheet to cause a sticky feeling, and the body fluid may flow back to a skin surface.

In addition, in the case of absorbing urine of a medium volume or more having a total urine volume of 20 cc or more, in the absorbent articles described in the above Patent Documents 1 and 2, there is concern that water may be retained in the surface sheet, and it is necessary to devise not to retain water on the surface sheet as much as possible.

Incidentally, in general, to improve a water retention property of the cotton nonwoven fabric, a material mixed with synthetic fiber which rarely retains water has been used rather than cotton. However, when synthetic fiber is mixed, there is a problem of degradation in touch which is a greatest feature of the cotton nonwoven fabric.

In this regard, a main object of the invention is to allow water absorbed in the surface sheet to rapidly permeate into the surface sheet without degrading flexibility in the absorbent article in which cotton nonwoven fabric is used as the surface sheet to obtain a soft tactile property.

As the invention according to claim 1 for solving the above-mentioned problems, provided is an absorbent article in which an absorber is interposed between a surface sheet and a back sheet, wherein the absorbent article is an incontinence pad having a medium volume or more for absorbing 20 cc or more of urine, and the surface sheet is formed by applying a water repellent to a spunlace nonwoven fabric containing 100 wt % of cotton fiber, a large number of openings penetrating obverse and reverse surfaces are formed at least in a section corresponding to an excretory opening, a heat-fusible fiber sheet is disposed adjacent to an absorber-side surface of the surface sheet, a plurality of adhesive portions is formed along a longitudinal direction of the absorbent article and at an interval in a widthwise direction thereof between the surface sheet and the heat-fusible fiber sheet, a compressed groove recessed from an outer surface side of the surface sheet to the absorber is formed close to the adhesive portion.

The invention described in claim 1 is targeted for an incontinence pad which absorbs urine caused by abdominal pressure incontinence instantaneously discharged when a force is applied to an abdomen, for example, at the time of sneezing, coughing, lifting a heavy object, etc. or urine caused by impending incontinence instantaneously discharged when an intense micturition desire is rapidly felt and may not be tolerated, and has a medium volume or more for absorbing 20 cc or more of a total urine volume. In the case of the incontinence pad, the incontinence pad is continuously used until the second incontinence in many cases, and the incontinence pad is worn for a long time in a state after the first incontinence and discharged after subsequent urination in many cases. Therefore, such an incontinence pad for a medium volume or more requires a function of instantaneously absorbing and holding a predetermined amount of urine and maintaining surface smoothness.

In addition, in an incontinence pad for a medium volume or more mainly for incontinence that occurs when a force is applied to an abdomen, urination does not occur when such a condition is not satisfied, the incontinence pad is worn for a long time in many cases. Therefore, in the absorbent article, a sheet formed by applying a water repellent to a spunlace nonwoven fabric containing 100 wt % of cotton fiber and provided with a large number of openings penetrating obverse and reverse surfaces formed at least in a section corresponding to an excretory opening is used as the surface sheet. For this reason, by adopting the spunlace nonwoven fabric containing 100 wt % of cotton fiber, a soft tactile property is obtained, and skin trouble at the time of wearing such as itching or rash can be hardly caused even after wearing for a long time. Water retention of the surface sheet which is a problem at that time is sufficiently improved by applying a water repellent and providing a large number of openings. Specifically, urine on the surface sheet is not absorbed by the surface sheet due to a water repellent treatment, and rapidly permeates the absorber from the openings, so that water is not retained in the surface sheet. When a formation region of the openings is formed not to include the section corresponding to the excretory opening, an incontinence range may not be covered, so that urine remains on the surface sheet to cause a sticky feeling, and skin trouble during wearing such as itching or rash is likely to occur.

Further, in the absorbent article, a heat-fusible fiber sheet is disposed adjacent to an absorber-side surface of the surface sheet, a plurality of adhesive portions is formed along a longitudinal direction of the absorbent article and at an interval in a widthwise direction thereof between the surface sheet and the heat-fusible fiber sheet, and a compressed groove recessed from an outer surface side of the surface sheet to the absorber is formed close to the adhesive portions. In this way, the body fluid is allowed to rapidly permeate the inside. That is, since the surface sheet and the heat-fusible fiber sheet are joined by the plurality of adhesive portions, a gap is rarely generated between the surface sheet and a sheet on the lower layer side. Further, by the surface sheet adhering to the heat-fusible fiber sheet, the body fluid absorbed in the surface sheet is rapidly transferred to the heat-fusible fiber sheet on the lower layer side. In addition, with regard to a permeability barrier of the body fluid due to an adhesive in the adhesive portion, the compressed groove recessed from the outer surface side of the surface sheet to the absorber is formed close to the adhesive portion to form a sparseness and denseness relationship of fiber such that a portion in which the compressed groove is formed has a higher fiber density than that of other portions, and the body fluid is drawn to the portion in which the compressed groove is formed and the fiber density is high from a portion in which the compressed groove is not formed and the fiber density is low using a capillary phenomenon of fiber. In this way, the body fluid is absorbed in the absorber in the part of the compressed groove, and thus the amount of water retention of the surface sheet is reduced.

As the invention according to claim 2, provided is the absorbent article according to claim 1, wherein the compressed groove is formed between adjacent adhesive portions.

In the invention described in claim 2, since the compressed groove is formed between the adjacent adhesive portions, a permeability barrier of the body liquid in these adhesive portions may be prevented.

As the invention according to claim 3, provided is the absorbent article according to claim 1 or 2, wherein a clearance between the adhesive portions and the compressed groove is 5 mm or less.

In the invention described in claim 3, by setting the clearance between the adhesive portions and the compressed groove to 5 mm or less, a high-density region of the fiber by the compressed groove and the adhesive portions are provided close to each other to surely prevent the permeability barrier of the body fluid due to the adhesive.

As the invention according to claim 4, provided is the absorbent article according to anyone of claims 1 to 3, wherein an adhesive is intermittently applied within a predetermined region or applied over an entire surface in the adhesive portions.

In the invention described in claim 4, as an application method of the adhesive in the adhesive portions, intermittent application within the predetermined region or overall application (solid application) is used. In the case of intermittent application, permeability of the body fluid in the adhesive portions can be ensured since the body fluid permeates through a non-application portion of the adhesive, and the permeability barrier of the body fluid in the adhesive portions is improved. Meanwhile, in the case of overall application, since joining strength between the surface sheet and the heat-fusible fiber sheet increases, adhesion between the surface sheet and the heat-fusible fiber sheet increases, a gap is rarely generated therebetween, and permeability of the body fluid from the surface sheet to the heat-fusible fiber sheet is improved.

As the invention according to claim 5, provided is the absorbent article according to anyone of claims 1 to 4, wherein the adhesive portions are formed in a range including the section corresponding to the excretory opening in the longitudinal direction of the absorbent article.

In the invention described in claim 5, to allow the body fluid to easily permeate the heat-fusible fiber sheet from the surface sheet in the section corresponding to the excretory opening, the adhesive portions are formed in a range including the section corresponding to the excretory opening in the longitudinal direction of the absorbent article.

As the invention according to claim 6, provided is the absorbent article according to any one of claims 1 to 5, wherein an adhesive is applied to the adhesive portions over an entire surface within a plurality of regions linearly extending along the longitudinal direction of the absorbent article and formed at an interval in the widthwise direction, and the compressed groove is formed in a pattern in which a recess and a protrusion are repeated in the widthwise direction of the absorbent article.

In the invention described in claim 6, when the adhesive portions are formed by overall application of the adhesive within a region linearly extending along the longitudinal direction of the absorbent article, the compressed groove is preferably formed in a pattern in which a recess and a protrusion are repeated in the widthwise direction of the absorbent article. In the case in which the compressed groove is linearly formed along the longitudinal direction of the absorbent article parallel to the adhesive portions, there is a high possibility that an inner surface of the compressed groove will be covered with the adhesive portions over the entire groove length when the compressed groove and the adhesive portion overlap each other due to a positional shift, etc. during operation, and there is concern that permeability of the body fluid in the compressed groove may be completely lost. On the other hand, in the case in which the compressed groove is formed in an uneven pattern in which a recess and a protrusion are repeated in the widthwise direction of the absorbent article as in the invention, even though a part of the compressed groove may overlap the adhesive portions due to a positional shift, etc. during operation, a groove bottom of the compressed groove is not covered with the adhesive portions over the entire groove length, and permeability of the body fluid in the compressed groove may be ensured.

As the invention according to claim 7, provided is the absorbent article according to any one of claims 1 to 6, wherein a second adhesive portion is formed in a region overlapping the adhesive portions in a thickness direction of the absorbent article between the heat-fusible fiber sheet and the absorber.

In the invention described in claim 7, a region overlapping the adhesive portions, which attach the surface sheet and the heat-fusible fiber sheet to each other, in the thickness direction of the absorbent article is set as a position of the second adhesive portion at which the heat-fusible fiber sheet and the absorber are attached to each other. In this way, the penetration barrier of the body fluid due to the adhesive is more unlikely to occur, and the body fluid transferred from the surface sheet to the heat-fusible fiber sheet is easily transferred to the absorber.

As described above, according to the invention, in an absorbent article in which cotton nonwoven fabric is used as a surface sheet to obtain a soft tactile property, it is possible to allow water absorbed in the surface sheet to rapidly permeate into the surface sheet without degrading flexibility.

BRIEF DESCRIPTION OF THE DRAWINGS

FIG. 1 is a partially cutaway development view of an incontinence pad 1 according to the invention.

FIG. 2 is an arrow view taken along line II-II of FIG. 1.

FIG. 3 is an enlarged cross-sectional view of an adhesive portion 20 and a compressed groove 21.

FIG. 4 is a plan view of an incontinence pad 1 according to a modification.

FIG. 5 is an enlarged plan view of an adhesive portion 20 and a compressed groove 21.

FIG. 6 is an arrow view taken along line VI-VI of FIG. 5.

FIG. 7 is a pattern of an adhesive portion and a compressed groove not included in the invention.

FIG. 8 is an arrow view taken along line VIII-VIII of FIG. 7.

FIG. 9 is a cross-sectional view of an incontinence pad 1 according to a modification.

FIG. 10 is a plan view of an incontinence pad 1 according to a modification.

FIG. 11 is an arrow view taken along line XI-XI of FIG. 10.

FIG. 12 is an enlarged plan view of a surface sheet 3.

FIG. 13 is a development view illustrating a water repellent application pattern on a surface of the surface sheet 3.

DETAILED DESCRIPTION

Hereinafter, embodiments of the invention will be described in detail with reference to drawings. The invention is an incontinence pad 1 for medium volume or more suitable for absorbing total urine volume of 20 cc or more, and is particularly suitable to absorb urine caused by abdominal pressure incontinence instantaneously discharged when a force is applied to an abdomen, for example, at the time of sneezing, coughing, lifting a heavy object, etc. or urine caused by impending incontinence instantaneously discharged when an intense micturition desire is rapidly felt and may not be tolerated.

<One Example of Basic Structure of Incontinence Pad>

As illustrated in FIG. 1 and FIG. 2, the incontinence pad 1 according to the invention mainly includes a liquid impermeable back sheet 2 made of a polyethylene sheet, a polypropylene sheet, etc., a surface sheet 3 forming a skin-contact surface and allowing rapid permeation of urine, etc., an absorber 4 made of cotton-like pulp, synthetic pulp, etc. and interposed between both the sheets 2 and 3, a heat-fusible fiber sheet 6 disposed adjacent to a surface of the surface sheet 3 on the absorber 4 side, and side nonwoven fabrics 7 and 7 arranged along a longitudinal direction in both side portions of a surface, respectively. In addition, in front and back end edge portions in the longitudinal direction of the pad around the absorber 4, outer edge portions of the liquid impermeable back sheet 2 and the surface sheet 3 are joined by an adhesive such as a hot melt or joining means such as heat sealing or ultrasonic sealing. In addition, in both side edge portions thereof, the liquid impermeable back sheet 2 laterally extending from a side edge of the absorber 4 and the side nonwoven fabric 7 are joined by an adhesive such as a hot melt or joining means such as heat sealing or ultrasonic sealing, and an outer peripheral flap portion in which the absorber 4 is not present is formed on an outer periphery thereof. To maintain a shape of the absorber 4 and to improve diffusibility, the absorber 4 may be surrounded by a wrapping sheet (not illustrated) made of crepe paper, nonwoven fabric, etc.

Hereinafter, the structure of the incontinence pad 1 will be further described in detail.

As the liquid impermeable back sheet 2, a sheet material having at least a water-blocking property such as an olefin-based resin sheet such as polyethylene or polypropylene is used. However, in addition thereto, it is possible to use a laminated nonwoven fabric obtained by laminating a nonwoven fabric on a polyethylene sheet etc, or a nonwoven fabric sheet (in this case, a liquid impermeable back sheet includes a waterproof film and a nonwoven fabric) after substantially ensuring liquid impermeability through the waterproof film. In recent years, a sheet material having moisture permeability tends to be used from a viewpoint of preventing stuffiness. This sheet material having the water-blocking property and the moisture permeability is a microporous sheet obtained by melt-kneading inorganic filler in an olefin-based resin such as polyethylene or polypropylene to mold a sheet, and then stretching the sheet in a uniaxial direction or biaxial direction.

In the illustrated example, a width of the surface sheet 3 is slightly wider than a width of the absorber 4 and merely covers the absorber 4, and an outer side of the surface sheet 3 in a widthwise direction is covered by the side nonwoven fabrics 7 (a member different from the surface sheet 3) extending from both side surfaces of the surface sheet 3.

As the side nonwoven fabric 7, it is possible to use a nonwoven fabric material subjected to an appropriate water-repellent treatment or hydrophilic treatment depending on the purpose of preventing penetration of urine, etc. or enhancing feeling of touch. As the side nonwoven fabric 7, it is possible to use a fabric formed by an appropriate processing method using natural fiber, synthetic fiber, regenerated fiber, etc. as a material, and it is preferable to use a nonwoven fabric having a suppressed basis weight and air permeability to eliminate a stiff feeling and prevent stuffiness. Specifically, it is desirable to use a nonwoven fabric manufactured by setting a basis weight to 15 to 23 g/m$^2$, and a water-repellent treated nonwoven fabric coated with a silicon-based or paraffin-based water repellent, etc. to surely prevent permeation of a body fluid is suitably used.

Although not illustrated, a part of the side nonwoven fabrics 7 and 7 may be laterally extended, and a wing-shaped flap may be formed together with a part of the liquid impermeable back sheet 2 which is similarly laterally extended. Further, the side nonwoven fabric 7 may be folded back to an inner side, and one or a plurality of threadlike elastically stretchable members may be arranged at a predetermined position, thereby forming a three-dimensional gather in which an inner side portion of the side nonwoven fabric is erected to a front surface side by a contracting force thereof.

<Surface Sheet 3>

The surface sheet 3 forms the skin-contact surface which is a part covering a skin side of the absorber 4, and is characterized by including a spunlace nonwoven fabric made of 100% by weight of cotton fiber. The spunlace nonwoven fabric has advantages that an adhesive is not used and the spunlace nonwoven fabric has flexibility.

The nonwoven fabric of the surface sheet 3 uses cotton fiber alone and does not contain synthetic fiber. As the cotton fiber, it is possible to use various cotton fibers such as raw cotton of a cotton plant, refined/bleached cotton fiber, cotton fiber dyed after being refined/bleached, refined/bleached absorbent cotton fiber, and recovered wool obtained by defibrating yarn or fabric, and it is particularly preferable to use non-absorbent cotton slightly having water repellency even in a fiber state due to natural fat and oil of cotton wax attached to a surface of cotton fiber.

It is preferable that a basis weight of the surface sheet 3 is set to 20 to 40 g/m$^2$, preferably 27 to 34 g/m$^2$, more preferably 29 to 32 g/m$^2$, and a thickness thereof is set to 0.25 to 0.50 mm, preferably 0.3 to 0.4 mm. The basis weight is calculated by measuring a weight of 5 cm×30 cm×10 sheets using an electronic balance and performing square meter conversion. In addition, the thickness is obtained in accordance with JIS-L1913.

In the surface sheet 3, a large number of openings penetrating obverse and reverse surfaces are provided at least in a section corresponding to an excretory opening to enhance liquid permeability. Specifically, the opening may be formed by supporting a fiber material on a mesh-like support in a hydroentanglement process at the time of manufacturing spunlace. In this case, by changing a condition of the mesh to be used, it is possible to adjust a size of each opening and an opening ratio. The openings may be formed by performing punching (die cutting) on a nonwoven fabric after manufacture. The opening may be provided on the entire surface sheet, and is preferably provided at least in the section corresponding to the excretory opening and the vicinity thereof. Preferably, the opening is provided in a region of 15% or more of the absorber length in a product length direction and 50% or more of the absorber width in a product widthwise direction including the section corresponding to the excretory opening, more preferably in a region of 50% or more of the absorber length in the product length direction and 70% or more of the absorber width in the product widthwise direction including the section corresponding to the excretory opening. When the formation region of the openings is less than 15% of the absorber length in the product length direction and less than 50% of the absorber width in the product widthwise direction, an incontinence range may not be covered, urine remains on the surface sheet 3, a sticky feeling is felt, and skin trouble at the time of wearing such as itching or rash easily occurs. When a sheet in which the large number of openings penetrating obverse and reverse surfaces are formed at least in the section corresponding to the excretory opening is used as the surface sheet 3, the body fluid rapidly permeates the surface sheet through the openings, and a problem that liquid remains on the surface is improved.

As illustrated in FIG. 12, the opening 10 is formed in a vertically long shape which is long in the longitudinal direction of the incontinence pad 1. For this reason, the body fluid easily permeates therethrough when compared to a circular opening, so that urine easily passes through the surface sheet 3 through the opening 10, and water retention to the surface sheet 3 is reduced. In addition, since the body fluid escapes while being deformed to be vertically long when urine passes through the opening 10, a diffusion direction of urine may be controlled in the longitudinal direction of the pad, diffusion in a lateral direction is suppressed, and lateral leakage rarely occurs. In the case of the spunlace, while an opening shape tends to be non-uniform, the shape of the opening 10 becomes a shape such as an approximately rectangular shape, a corner-eliminating and elongated hole shape, or an elliptical shape.

With regard to dimensions of the opening 10, it is desirable that a length L1 of the incontinence pad 1 in the longitudinal direction is 1.0 to 4.0 mm, preferably 1.5 to 3.0 mm, and a length L2 of the incontinence pad 1 in the widthwise direction is 0.5 to 1.5 mm, preferably 0.5 to 1.0 mm. When a dimension of the opening 10 is less than 0.5 mm, urine hardly passes through, and it is difficult to form a clear opening due to fluffing of the fiber. When a maximum dimension of the opening 10 exceeds 4.0 mm, a liquid from the opening 10 flows back, which causes surface exposure of a constituent material of the absorber 4. In addition, it is desirable that a ratio (L1/L2) of L1 to L2 is set to 1.2 to 5.0, preferably 2.0 to 3.0. It is desirable that an area A of the opening 10 is set to 0.9 to 3.0 mm$^2$, preferably 0.9 to 2.5 mm$^2$. Further, it is desirable that the opening ratio is set to 15 to 45%, preferably 17 to 30%, more preferably 18 to 25%. The dimensions of the opening 10 may not be uniform over the whole area, and the opening 10 may be formed in an arbitrary size as long as the size falls within the above-mentioned range.

As illustrated in FIG. 12, the surface sheet 3 has a structure in which a plurality of vertical stripes 11, 11, . . . extending along the longitudinal direction of the incontinence pad 1 and formed at an interval in the widthwise direction and a plurality of horizontal stripes 12, 12, . . . extending along the widthwise direction of the incontinence pad 1, formed at an interval in the longitudinal direction, and connecting adjacent vertical stripes 11 and 11 to each other are formed by the cotton fiber, and the opening 10 is formed in a part surrounded by the vertical stripe 11 and the horizontal stripe 12.

It is desirable that a width W1 of the vertical stripe 11 is set to 0.5 to 2.5 mm, preferably 0.8 to 2.3 mm, and a width W2 of the horizontal stripe 12 is set to 0.2 to 1.6 mm, preferably 0.3 to 1.4 mm. In addition, it is desirable that a ratio (W1/W2) of the width W1 to the width W2 is set to 1.2 to 2.0, preferably 1.5 to 2.0. When the width W1 of the vertical stripe 11 is set to be larger than the width W2 of the horizontal stripe 12, liquid diffusion in the longitudinal direction of the incontinence pad 1 along the vertical stripe 11 is likely to occur.

The vertical stripe 11 is formed to have a larger fiber amount and higher density when compared to the horizontal stripe 12. In this way, only a part of the vertical stripe 11 comes into contact with the skin, a contact area with respect to the skin is reduced, and occurrence of skin trouble during wearing such as itching or rash may be suppressed after wearing for a long time. At the same time, a sticky feeling is reduced after incontinence. In addition, when urine passes through the surface sheet 3, diffusion in the longitudinal direction of the incontinence pad 1 along the vertical stripe 11 having relatively high density is likely to occur due to the capillary phenomenon of the fiber. Furthermore, since a diffusion direction of urine passing through the opening 10 and a diffusion direction of urine permeating through the surface sheet 3 coincide with each other in the longitudinal direction of the incontinence pad 1, penetration into the vertical stripe 11 of the surface sheet 3 occurs by being drawn into urine passing through the opening 10. Thus, residual liquid of the surface sheet 3 is suppressed as much as possible.

Measurement of the fiber amount can be carried out in accordance with "sieve-analysis test method of paper pulp" of JIS P8207. Further, measurement of the density can be carried in accordance with JIS P8118 "thickness and density test method".

A water repellent is externally added and applied to the surface sheet 3. As the water repellent, it is possible to appropriately select and use a water repellent less irritating to the skin among known water repellents such as a paraffin-based water repellent and a silicone-based water repellent, and it is more preferable to appropriately select and use oil and fat less irritating to the skin such as glyceryl stearate, stearic acid amide, zinc stearate, calcium stearate, diethanol amide stearate, or magnesium stearate. Among these materials, glyceryl stearate is particularly preferable. When a water repellent made of glyceryl stearate is used in the incontinence pad 1, a coating amount thereof is preferably set to 0.05 to 0.30 parts by weight with respect to 100 parts by weight of the fibers (in the case of double-sided coating, a total coating amount on both sides). A more preferable coating amount is 0.08 to 0.25 parts by weight. When the coating amount of the water repellent is less than 0.05 parts by weight, a water repellent effect may be insufficient in some cases. When the coating amount exceeds 0.30 parts by weight, the water repellency is excessively high, and moisture is rather difficult to permeate.

The water repellent may be applied only to the skin-contact surface or both the skin-contact surface and the surface on the absorber 4 side. However, it is desirable that at least a water absorption amount obtained from a water absorption amount test described below is 0.03 g or less, suitably 0.02 g or less.

An absorption amount of the surface sheet 3 may be obtained according to the following procedure. (1) A sample of 10 cm square is prepared, and a weight is measured (A). (2) Three paper filters of 10 cm square are stacked such that a smooth side faces upward, and the sample is set thereon. (3) 3 ml of room temperature tap water is dropped onto the set sample, and the sample is left for five minutes. (4) A weight of the sample after five minutes of leaving is measured (B). (5) The absorption amount (water retention amount) of the surface sheet 3 is obtained by (B)−(A)= absorption amount (g).

In particular, it is more preferable that the water absorbency of the surface of the surface sheet 3 on the absorber 4 side is higher than the water absorbency of the skin-contact surface. Therefore, it is desirable that the water absorbency on the skin-contact surface side (JIS L1907 Byreck method) is set to 0 mm to 5 mm, preferably 0 mm to 2 mm, and the water absorbency of the surface on the absorber 4 side (JIS L1907 Byreck method) is set to 0 mm to 10 mm, particularly preferably about 2 mm to 4 mm. Such a difference in water absorbency can be easily obtained by applying the water repellent to only the skin-contact surface of the surface sheet 3. However, the water repellent may be applied to both surfaces of the surface sheet 3. In this case, a smaller amount than that on the skin-contact surface is applied to the surface on the absorber 4 side. Even when the water repellent is applied only to the skin-contact surface of the surface sheet 3, the surface on the absorber 4 side has water repellency depending on the thickness and the basis weight. Whether the application surface of the water repellent is set to one surface or both surfaces, and a ratio of the coating amount on the both surfaces in a case in which the application surface is set to the both surfaces are appropriately selected so that liquid permeability and absorbency can be maintained in a well-balanced manner together with conditions such as the thickness, the basis weight, and the opening of the surface sheet 3.

Known methods such as transfer, spraying, brush coating, impregnation, and dipping can be appropriately used as a coating method for the water repellent. In the case of imparting a difference in water absorbency on both sides of the sheet, a coating method by transfer can be preferably used.

The water repellent is preferably applied on the entire surface from a viewpoint of manufacturing efficiency. However, it is sufficient that the water repellent is applied at least to the section H corresponding to the excretory opening, and the water repellent may be applied only to a part receiving the excreted liquid. For example, as illustrated in FIG. 13(A), a water repellent application part 40 may be provided except for both side portions in the widthwise direction. Alternatively, as illustrated in FIG. 13(B), the water repellent application part 40 may be provided only in a central part in the widthwise direction and a middle part in a front-back direction.

<Absorber 4>

The absorber 4 is capable of absorbing and retaining urine, and a superabsorbent polymer in the form of powder is dispersed and mixed in fluff-like pulp fiber and used as the absorber 4. The absorber 4 is made of only pulp fiber and the superabsorbent polymer and does not contain synthetic fiber.

Examples of the pulp fiber include a cellulose fiber such as chemical pulp or dissolved pulp obtained from wood and an artificial cellulose fiber such as rayon or acetate. Softwood pulp having a longer fiber length than that of hardwood pulp is suitably used in terms of function and price.

It is desirable that a basis weight of the pulp fiber is set to 75 to 300 g/m$^2$, preferably 155 to 270 g/m$^2$, and it is desirable that a basis weight of the superabsorbent polymer is set to 85 to 185 g/m$^2$, preferably 100 to 165 g/m$^2$.

Examples of the superabsorbent polymer include cross-linked polyacrylate, self-crosslinked polyacrylate, a saponified product of a crosslinked product of an acrylic acid ester-vinyl acetate copolymer, a crosslinked product of an isobutylene/maleic anhydride copolymer, a crosslinked product of polysulfonate, and a partially crosslinked water-swelling polymer such as polyethylene oxide or polyacrylamide. Among these examples, acrylic acid or acrylate salt-based one which is excellent in absorption amount and absorption rate is suitable. In the manufacturing process, an absorption ratio (absorption power) and an absorption rate of the superabsorbent polymer having absorbing performance may be adjusted by adjusting crosslink density and crosslink density gradient.

It is desirable that a ratio of the pulp fiber to the superabsorbent polymer is set to pulp fiber:superabsorbent polymer=70 to 30% by weight:30 to 70% by weight, preferably 62 to 45% by weight:38 to 55% by weight, more preferably 60 to 50% by weight:40 to 50% by weight.

In the incontinence pad 1, since each of the pulp fiber and the superabsorbent polymer is configured at a predetermined basis weight, and an absorber in which the pulp fiber and the superabsorbent polymer are configured at a predetermined weight ratio is used, the pulp fiber having a high absorption rate rapidly absorbs urine immediately after urination even when urine is instantaneously discharged, and then it is possible to completely prevent back flow to the surface when urine absorbed by this pulp fiber is gradually absorbed and retained in the superabsorbent polymer.

On the other hand, when the pulp fiber is more than 70% by weight, and the superabsorbent polymer is less than 30% by weight, a content ratio of the pulp fiber becomes high. Thus, the liquid retaining property of the absorber 4 is low, and back flow is likely to occur in the surface sheet 3 after urination. Meanwhile, when the pulp fiber is less than 30% by weight, and the superabsorbent polymer is more than 70% by weight, a content ratio of the superabsorbent polymer becomes high. Thus, an initial absorption rate immediately after urination is slow, transfer of urine from the surface sheet 3 to the absorber 4 is not smoothly performed, and liquid tends to remain on the surface sheet 3 immediately after urination.

In addition, urine is surely absorbed and retained in the absorber immediately after urination, and the liquid does not remain in the surface sheet. Thus, it is possible to suppress spreading of a urine diffusion range in the surface sheet.

The absorber 4 is preferably surrounded by a package sheet such as crepe paper for shape retention and polymer powder retention.

<Heat-Fusible Fiber Sheet 6>

In the incontinence pad 1, the heat-fusible fiber sheet 6 is interposed between the absorber 4 and the surface sheet 3 adjacent to the surface of the surface sheet 3 on the absorber 4 side. As heat-fusible fiber contained in the heat-fusible fiber sheet 6, it is possible to use arbitrary fiber which dissolves by heating and develops mutual adhesiveness. This heat-fusible fiber may contain a single fiber or correspond to a composite fiber obtained by combining two or more types of synthetic resins. Specifically, it is possible to use polyolefin-based single fibers such as polyethylene, polypropylene and polyvinyl alcohol, a sheath-core type composite fiber or an eccentric sheath-core type composite fiber in which a sheath portion made of polyethylene terephthalate/polyethylene, polyethylene terephthalate/polypropylene, polypropylene/polyethylene, polyethylene terephthalate-ethylene/polypropylene copolymer, low melting point polyester-polyester, etc. is set to have a relatively low melting point, a split type composite fiber in which a part of each component made of polyethylene terephthalate/polypropylene, polyethylene terephthalate/nylon, and polypropylene/polyethylene is exposed to a surface, or a heat split type composite fiber split by heat shrinkage of one component made of a polyethylene terephthalate/ethylene-propylene copolymer. In this case, the sheath-core type composite fiber is preferable in the case of placing importance on productivity and dimensional stability, and an eccentric type composite fiber is preferable when volume sense of the nonwoven fabric is emphasized. In addition, when flexibility is emphasized, and the split type composite fiber or the heat split type composite fiber is used, each component is easily divided into ultrafine fibers at the time of high pressure water flow treatment for entangling fibers.

It is desirable that the heat-fusible fiber sheet 6 has a basis weight set to a range of 10 to 50 $g/m^2$, preferably 20 to 40 $g/m^2$, and a fiber thickness set to 4 to 7 dt, preferably 5 to 6 dt from a viewpoint of texture, skin touch, etc.

The heat-fusible fiber sheet 6 preferably has a lower fiber density (coarse mesh) than that of cotton nonwoven fabric contained in the surface sheet 3 and hydrophilicity. To impart hydrophilicity to the heat-fusible fiber sheet 6, it is possible to use a nonwoven fabric to which hydrophilicity is imparted by surface-treating a synthetic fiber such as an olefin-based fiber such as polyethylene or polypropylene, a polyester-based fiber, or a polyamide-based fiber using a hydrophilizing agent. Among these materials, in particular, it is preferable to use an air-through nonwoven fabric or a spunbond nonwoven fabric. When the air-through nonwoven fabric or the spunbond nonwoven fabric which is relatively soft and bulky is used, a cushioning characteristic is given, a wearing feeling is improved, and water retention capacity increases.

In addition, it is desirable that the heat-fusible fiber sheet 6 is formed to have a lower fiber density than that of cotton nonwoven fabric contained in the surface sheet 3. In this way, when a compressed groove 21 is provided, cotton fiber of the cotton nonwoven fabric easily enters the inside of the heat-fusible fiber sheet 6, and the body fluid rapidly permeates into the heat-fusible fiber sheet 6 from the cotton nonwoven fabric.

As illustrated in FIG. 1 and FIG. 2, planar dimensions of the heat-fusible fiber sheet 6 are substantially the same as those of the surface sheet 3. That is, the heat-fusible fiber sheet 6 is arranged over substantially the whole length from a front end to the rear end of the incontinence pad 1 in the longitudinal direction of the incontinence pad 1 and has a slightly wider width than the width of the absorber 4 to merely cover the absorber 4 in the widthwise direction of the incontinence pad 1, and outer sides of the surface sheet 3 and the heat-fusible fiber sheet 6 in the widthwise direction are covered by the side nonwoven fabrics 7 (a member different from the surface sheet 3 and the heat-fusible fiber sheet 6) extending from the both side surfaces of the surface sheet 3.

<With Regard to Adhesive Portion and Compressed Groove>

In the incontinence pad 1, a plurality of adhesive portions 20, 20, . . . is formed along the longitudinal direction of the incontinence pad 1 and at an interval in the widthwise direction between the surface sheet 3 and the heat-fusible fiber sheet 6, and a compressed groove 21 integrally recessed from the outer surface side of the surface sheet 3 to the absorber 4 is formed close to the adhesive portion 20.

In the incontinence pad 1, since the surface sheet 3 and the heat-fusible fiber sheet 6 are joined together by the plurality of adhesive portions 20, 20, . . . , a gap is rarely generated between the surface sheet 3 and the heat-fusible fiber sheet 6. Further, the body fluid absorbed in the surface sheet 3 is rapidly transferred to the heat-fusible fiber sheet 6 on the lower layer side by the surface sheet 3 adhering to the heat-fusible fiber sheet 6. In addition, with regard to a permeability barrier of the body fluid due to an adhesive in the adhesive portion 20, the compressed groove 21 recessed from the outer surface side of the surface sheet 3 to the absorber 4 is formed close to the adhesive portion 20 to form a sparseness and denseness relationship of fiber such that a portion in which the compressed groove 21 is formed has a higher fiber density than that of other portions, and the body fluid is drawn to the portion in which the compressed groove 21 is formed and the fiber density is high from a portion in which the compressed groove 21 is not formed and the fiber density is low using a capillary phenomenon of fiber. In this way, the body fluid is absorbed in the absorber 4 in the part of the compressed groove 21, and thus the amount of water retention of the surface sheet 3 is reduced.

The adhesive portion 20 joins the surface sheet 3 and the heat-fusible fiber sheet 6, and thus corresponds to a range including an application portion of a hot melt adhesive formed between the surface sheet 3 and the heat-fusible fiber sheet 6. When the adhesive is applied on the entire surface, a range in which this adhesive is applied corresponds to the adhesive portion 20. When both an application portion and a non-application portion of the adhesive are present, a predetermined range surrounding the application portion of the adhesive corresponds to the adhesive portion 20.

The adhesive portion 20 is preferably formed in a shape of two or more stripes along the longitudinal direction of the incontinence pad 1 and at an interval in the widthwise direction. In the example illustrated in FIG. 1, the adhesive portion 20 is formed in a shape of four stripes along the longitudinal direction of the incontinence pad 1 and at an interval in the widthwise direction. An interval of adjacent adhesive portions 20 and 20 in the pad widthwise direction may be an equal width. However, in the example of FIG. 1, the interval is relatively wide in a central portion of the incontinence pad 1 in the widthwise direction and relatively narrow on both sides thereof. A relatively wide interval is provided in the central portion in the widthwise direction to ensure permeability of the body fluid in the central portion in the widthwise direction.

In the adhesive portion 20, it is possible to adopt intermittent application in which both the application portion and the non-application portion of the adhesive are present within the predetermined region, or it is possible to adopt overall application (solid application) in which the non-application portion is not included and the adhesive is applied over the entire surface. Examples of coating of the adhesive include spiral coating, porous coating, spray coating, curtain coating, and slot coating. In the example illustrated in FIG. 1, the adhesive is coated in spiral coating. In the case of intermittent application, permeability of the body fluid in the adhesive portion 20 can be ensured through the non-application portion of the adhesive, and the permeability barrier of the body fluid in the adhesive portion 20 is improved. Meanwhile, in the case of overall application, joining strength between the surface sheet 3 and the heat-fusible fiber sheet 6 increases, adhesion between the surface sheet 3 and the heat-fusible fiber sheet 6 increases, a gap is rarely generated therebetween, and permeability of the body fluid from the surface sheet 3 to the heat-fusible fiber sheet 6 is improved.

The adhesive portion 20 is formed in a range including the section corresponding to the excretory opening in the longitudinal direction of the incontinence pad 1. In the example illustrated in FIG. 1, the adhesive portion 20 is formed to connect front and rear end edges of the incontinence pad 1 over the entire length of the incontinence pad 1. In this way, the surface sheet 3 and the heat-fusible fiber sheet 6 may adhere to each other over the entire length, and permeability of the body fluid from the surface sheet 3 to the heat-fusible fiber sheet 6 may be enhanced over the entire length of the sheet.

In addition, as illustrated in FIG. 4, the adhesive portion 20 may include the section corresponding to the excretory opening and be in a range slightly longer than the section in forward and backward directions, so that the adhesive portion 20 may not be formed in each of front and back end portions of the incontinence pad 1. When adhesion between the surface sheet 3 and the heat-fusible fiber sheet 6 by the adhesive portion 20 can be enhanced at least in the section corresponding to the excretory opening, permeability can be ensured in an incontinence range. At this time, the adhesive portion 20 is preferably in a range slightly longer than the compressed groove 21 in the forward and backward directions.

In the incontinence pad 1, since a sheet in which the large number of openings 10, 10, . . . penetrating obverse and reverse surfaces are formed at least in the section corresponding to the excretory opening is used as the surface sheet 3, it is desirable to use a hot melt adhesive having a predetermined condition as an adhesive included in the adhesive portion 20 so that the adhesive included in the adhesive portion 20 does not come out to the surface through the opening 10 of the surface sheet 3. This hot melt adhesive is preferably applied with a basis weight of 1 to 20 g/m$^2$, preferably 2 to 9 g/m$^2$. In addition, even though a type of hot melt adhesive is not particularly limited, it is preferable to use an olefin-based one such as polyethylene, polypropylene, or an ethylene-α-olefin copolymer, an ethylene-vinyl acetate copolymer-based one, a polyamide-based one, a thermoplastic elastomer-based one such as a styrene-butylene-styrene copolymer or a styrene-isoprene-styrene copolymer, etc.

The compressed groove 21 is compressed from the surface side of the surface sheet 3 by passing between an embossing roll provided with a plurality of protruding embossed protrusions on a peripheral surface and an anvil roll having a flat surface in a state in which the heat-fusible fiber sheet 6 and the surface sheet 3 are laminated on the skin side of the absorber 4, and is obtained by integrally recessing a member from the outer surface side of the surface sheet 3 to the absorber 4 to a non-skin side by joining the surface sheet 3 and the heat-fusible fiber sheet 6 by heat sealing of the heat-fusible fiber sheet 6. The surface sheet 3 contains cotton nonwoven fabric, and thus a shape of a recessed groove by compression is hardly maintained by the surface sheet 3 alone. However, when the surface sheet 3 is compressed together with the heat-fusible fiber sheet 6, the melted heat-fusible fiber permeates the surface sheet 3 and fuses, and thus a compressed state of the surface sheet 3 is maintained.

The compressed groove 21 is formed in the section corresponding to the excretory opening and the vicinity thereof. The compressed groove 21 may be formed in each of both side portions of the section corresponding to the excretory opening along the longitudinal direction of the incontinence pad 1. In the example illustrated in FIG. 1, the compressed groove 21 is formed in a substantially elliptical shape or oval shape in planar view surrounding the section corresponding to the excretory opening and including a portion linearly extending along the longitudinal direction of the incontinence pad 1 and a portion extending along the widthwise direction to connect front and rear end portions of both side portions in each of the both side portions of the section corresponding to the excretory opening. In the compressed groove 21, the portion linearly extending along the longitudinal direction in the both side portions is formed between adjacent adhesive portions 20 and 20, and the portion connecting front and rear end portions of the linearly extending portion and extending along the widthwise direction is formed to traverse the adhesive portion 20.

It is desirable that the compressed groove 21 is formed close to the adhesive portion 20 in a spaced portion of adhesive portions 20 and 20 in which the adhesive portion 20 is not formed between adjacent adhesive portions 20 and 20 spaced apart in the pad widthwise direction. When the compressed groove 21 is formed between the adjacent adhesive portions 20 and 20, it is possible to simultaneously prevent a permeability barrier of the body fluid due to these adhesive portions 20 and 20.

In addition, it is preferable that the adhesive portion 20 and the compressed groove 21 are formed to have a predetermined clearance U. Specifically, as illustrated in FIG. 1 and FIG. 3, it is desirable that the clearance U between the adhesive portion 20 and the compressed groove 21 is set to 5 mm or less, preferably 3 mm or less, more preferably 1 mm or less and 0.5 mm or more. As a result, a high-density region due to the compressed groove 21 is formed at a predetermined position close to the adhesive portion 20. Thus, even when a penetration barrier of the body fluid from the surface sheet 3 to the heat-fusible fiber sheet 6 is generated in the adhesive portion 20, the body fluid is drawn to the compressed groove 21 by a capillary phenomenon due to a density difference between fibers, and absorbed and held by the absorber 4 through the compressed groove 21.

The clearance U can be measured by the following procedure. After the surface sheet 3 is peeled off in a state in which an adhesive is solidified by spraying a cold spray from the outer surface side of the surface sheet 3, a powdered color powder (toner) is scattered on the adhesive portion 20 and attached to the adhesive, and a distance between an end portion of the adhesive on a side close to the compressed groove 21 and an end portion of the compressed groove 21 on a side close to the adhesive portion 20 is measured using a ruler, etc.

When the most part of the compressed groove 21 in a groove widthwise direction and a groove longitudinal direction does not overlap the adhesive portion 20, a part of the compressed groove 21 may overlap the adhesive portion 20. Specifically, as illustrated in FIG. 1, in the adhesive portion 20 formed by spiral coating of the adhesive, even when the linearly extending compressed groove 21 overlaps the adhesive portion 20, a bottom surface and a side surface of the compressed groove 21 are not entirely covered by an adhesive application portion of the adhesive portion 20, and thus permeability of the body fluid in the compressed groove 21 is ensured. A ratio of the compressed groove 21 overlapping the adhesive portion 20 is desirably less than 50%, preferably less than 30% of a length of the compressed groove 21 extending in the pad longitudinal direction.

Meanwhile, as illustrated in FIG. 5 and FIG. 6, when the adhesive portion 20 linearly extends along the longitudinal direction of the incontinence pad 1, and an adhesive is applied over the entire surface within a plurality of stripe-shaped regions formed at an interval in the widthwise direction, the compressed groove 21 is preferably formed in a pattern in which a recess and a protrusion are repeated in the widthwise direction of the incontinence pad 1. In the case in which the compressed groove is linearly formed along the longitudinal direction of the incontinence pad 1 parallel to the adhesive portion, as illustrated in FIG. 7 and FIG. 8, there is a high possibility that an inner surface of the compressed groove will be covered with the adhesive portion over the entire groove length when the compressed groove and the adhesive portion overlap each other due to a positional shift, etc. during operation, and there is concern that permeability of the body fluid in the compressed groove may be completely lost. On the other hand, as illustrated in FIG. 5 and FIG. 6, in the case in which the compressed groove 21 is formed in an uneven pattern in which a recess and a protrusion are repeated in the widthwise direction of the incontinence pad 1, even though a part of the compressed groove 21 may overlap the adhesive portion 20 due to a positional shift, etc. during operation, a groove bottom of the compressed groove 21 is not covered with the adhesive portion 20 over the entire groove length, and permeability of the body fluid in the compressed groove 21 may be ensured. The pattern of the compressed groove 21 in which the recess and the protrusion are repeated in the widthwise direction of the incontinence pad 1 refers to a pattern in which a portion protruding to one side in the widthwise direction with respect to a line in the pad longitudinal direction and a portion protruding to the other side in the widthwise direction are alternately formed in the pad longitudinal direction.

Next, adhesion between the heat-fusible fiber sheet 6 and the absorber 4 will be described. As illustrated in FIG. 9, a second adhesive portion 22 may be formed in a region overlapping the adhesive portion 20 in a thickness direction of the incontinence pad 1 between the heat-fusible fiber sheet 6 and the absorber 4. That is, it is preferable that the second adhesive portion 22 joining the heat-fusible fiber sheet 6 and the absorber 4 together is formed only at a position overlapping the adhesive portion 20 joining the surface sheet 3 and the heat-fusible fiber sheet 6 together and is not formed in a portion other than the position overlapping the adhesive portion 20. In this way, the penetration barrier of the body fluid due to the adhesive is more unlikely to occur, and the body fluid transferred from the surface sheet 3 to the heat-fusible fiber sheet 6 is easily transferred to the absorber 4.

As an incontinence pad 1A according to a modification, as illustrated in FIG. 10 and FIG. 11, it is possible to form a compressed groove 21A along the longitudinal direction at least in a central portion of the section corresponding to the excretory opening in the pad widthwise direction and in an intermediate portion in the longitudinal direction. In this case, the compressed groove 21A receives discharged urine, temporarily stores urine in the compressed groove 21A, induces diffusion of urine in the front-back direction, increases an absorption speed of urine to the absorber 4, and prevents lateral leakage. Similarly to the compressed groove 21 according to the above embodiment, the compressed groove 21A is formed to be integrally recessed from the outer surface side of the surface sheet 3 to the absorber 4 in the vicinity of the adhesive portion 20.

The compressed groove 21A may be formed by integrally compressing a member from the surface sheet 3 to the absorber 4 from the outer surface side of the surface sheet 3. Alternatively, an absorber recess recessed toward a non-skin side surface may be previously formed in a portion in which the compressed groove 21A of the absorber 4 is to be formed, and the compressed groove 21A may be formed by integrally compressing a member from the outer surface side of the surface sheet 3 to the absorber 4 along the absorber recess. The latter one is desirable for a reason that deformation of the compressed groove 21A due to a leg pressure can be prevented.

When the compressed groove 21A is provided, transfer of the body fluid from the surface sheet 3 to the absorber 4 is promoted in the section corresponding to the excretory opening. Although not illustrated, in addition to the compressed groove 21A, it is possible to form the compressed groove 21 in each of the both side portions of the section corresponding to the excretory opening.

[Other Modifications]

As the absorber 4, it is possible to use an absorber having a multi-layer structure in which a plurality of layers is laminated. Specific examples may include an absorber having a two-layer structure including an upper-layer absorber and a lower-layer absorber. The absorber having the multi-layer structure may have a structure in which absorbers having the same planar shape are laminated or a structure in which a width dimension and a longitudinal dimension of the absorber on the upper layer side are smaller than those of the absorber on the lower layer side. For example, in the absorber having the two-layer structure, it is possible to adopt a structure in which the upper-layer absorber forms a middle-high portion of an absorber which is high to the skin side in the section corresponding to the excretory opening. In this case, it is preferable that the compressed groove 21 is provided to the lower-layer absorber to surround the middle-high portion (upper-layer absorber). Alternatively, the compressed groove 21 may be provided to integrally compress all the absorbers of the multi-layer structure, or provided to compress only some absorbers laminated on the upper layer side.

The invention claimed is:

1. An absorbent article in which an absorber is interposed between a surface sheet and a back sheet,
    wherein the absorbent article is an incontinence pad having an absorption capability of 20 cc or more of urine, and
    wherein the surface sheet is formed by applying a water repellent to a spunlace nonwoven fabric containing 100 wt % of cotton fiber,
    a large number of openings penetrating obverse and reverse surfaces of the surface sheet are formed at least in a section of the surface sheet corresponding to an excretory opening of a user when the article is worn by the user,
    a heat-fusible fiber sheet is disposed adjacent to an absorber-side surface of the surface sheet, a plurality of adhesive portions is formed along a longitudinal direction of the absorbent article and at an interval in a widthwise direction thereof between the surface sheet and the heat-fusible fiber sheet, and
    a compressed groove recessed from an outer surface side of the surface sheet and extending at least partially in a thickness direction into the absorber, is formed close to the adhesive portions.

2. The absorbent article according to claim 1, wherein the compressed groove is formed between adjacent adhesive portions.

3. The absorbent article according to claim 1, wherein a clearance between the adhesive portions and the compressed groove is 5 mm or less.

4. The absorbent article according to claim 1, wherein an adhesive is intermittently applied within a predetermined region or applied over an entire surface in the adhesive portions.

5. The absorbent article according to claim 1, wherein the adhesive portions are formed in a range including the section corresponding to the excretory opening in the longitudinal direction of the absorbent article.

6. The absorbent article according to claim 1,
    wherein an adhesive is applied to the adhesive portions over an entire surface within a plurality of regions linearly extending along the longitudinal direction of the absorbent article and formed at an interval in the widthwise direction, and
    the compressed groove is formed in a pattern in which a recess and a protrusion are repeated in the widthwise direction of the absorbent article.

7. The absorbent article according to claim 1, wherein a second adhesive portion is formed in a region overlapping the adhesive portions in a thickness direction of the absorbent article between the heat-fusible fiber sheet and the absorber.

8. The absorbent article according to claim 1, wherein the compressed groove undulates in a continuous manner over a longitudinal direction of the absorbent article, the compressed groove having undulations extending in a widthwise direction of the absorbent article.

* * * * *